(12) United States Patent
Crescini et al.

(10) Patent No.: US 10,429,367 B2
(45) Date of Patent: Oct. 1, 2019

(54) MULTI-PARAMETRIC ENVIRONMENTAL DIAGNOSTICS AND MONITORING SENSOR NODE

(71) Applicants: QATAR UNIVERSITY, Doha (QA); UNIVERSITA DEGLI STUDIO DE BRESCIA, Brescia (IT)

(72) Inventors: Damiano Crescini, Gussago (IT); Farid Touati, Kebili (TN); Paolo Crescini, Gussago (IT); Claudio Legena, Brescia (IT); Alessio Galli, Collebeato (IT); Adel Ben Mnaouer, Mirdif (AE)

(73) Assignees: Qatar University, Doha (QA); University of Brescia, Brescia (IT)

( * ) Notice: Subject to any disclaimer, the term of this patent is extended or adjusted under 35 U.S.C. 154(b) by 173 days.

(21) Appl. No.: 15/304,855

(22) PCT Filed: May 7, 2015

(86) PCT No.: PCT/US2015/029731
§ 371 (c)(1),
(2) Date: Oct. 17, 2016

(87) PCT Pub. No.: WO2015/171920
PCT Pub. Date: Nov. 12, 2015

(65) Prior Publication Data
US 2017/0184560 A1 Jun. 29, 2017

Related U.S. Application Data

(60) Provisional application No. 61/989,732, filed on May 7, 2014.

(51) Int. Cl.
*G01N 33/00* (2006.01)
*G01D 11/00* (2006.01)
(Continued)

(52) U.S. Cl.
CPC ......... *G01N 33/0037* (2013.01); *G01D 11/00* (2013.01); *G01D 21/02* (2013.01);
(Continued)

(58) Field of Classification Search
CPC ............... G01N 33/0037; G01N 27/26; G01N 33/0031; G01N 33/004; G01N 33/0044;
(Continued)

(56) References Cited

U.S. PATENT DOCUMENTS 4,916,934 A * 4/1990 Nagata ............... G01N 27/4077
204/428
6,252,510 B1 6/2001 Dungan
(Continued)

FOREIGN PATENT DOCUMENTS

WO WO 9960384 11/1999
WO WO 2012/056477 5/2012

*Primary Examiner* — Tarun Sinha
(74) *Attorney, Agent, or Firm* — Richard C. Litman

(57) ABSTRACT

The multi-parametric environmental diagnostics and monitoring sensor node (10) provides monitoring and diagnostics of a variety of different ambient environmental factors and is powered by multiple sources of renewable energy. The multi-parametric environmental diagnostics and monitoring sensor node (10) includes a base (38) and a plurality of environmental condition sensors (36a, 36b, 36c, 36d, 36e, 36f) mounted thereon. A controller (47) is also mounted on the base (38), the plurality of environmental condition sensors (36a, 36b, 36c, 36d, 36e, 36f) being in communication therewith. An external photovoltaic cell (18) is mounted to the base and an internal photovoltaic cell (34) is mounted in an opposed orientation on a cover (32). The external photovoltaic cell (18) and the internal photovoltaic cell (34) charge a power storage module (52), which powers the plurality of environmental condition sensors (36a, 36b, 36c, 36d, 36e, 36f) and the controller (47).

11 Claims, 6 Drawing Sheets

(51) Int. Cl.

| | |
|---|---|
| *G01D 21/02* | (2006.01) |
| *G01W 1/11* | (2006.01) |
| *H02S 40/38* | (2014.01) |
| *G01N 27/26* | (2006.01) |
| *H02J 7/35* | (2006.01) |
| *H02J 7/34* | (2006.01) |
| *G01L 19/00* | (2006.01) |

(52) U.S. Cl.
CPC ............ *G01N 27/26* (2013.01); *G01N 33/004* (2013.01); *G01N 33/0031* (2013.01); *G01N 33/0044* (2013.01); *G01N 33/0054* (2013.01); *G01N 33/0073* (2013.01); *G01W 1/11* (2013.01); *H02J 7/355* (2013.01); *H02S 40/38* (2014.12); *G01L 19/0092* (2013.01); *H02J 7/345* (2013.01)

(58) Field of Classification Search
CPC ............ G01N 33/0054; G01N 33/0073; H02S 40/38; G01D 11/00; G01D 21/02
USPC .......................................................... 73/29.01
See application file for complete search history.

(56) References Cited

U.S. PATENT DOCUMENTS

| | | |
|---|---|---|
| 2004/0056771 A1 | 3/2004 | Dungan |
| 2006/0173579 A1* | 8/2006 | Desrochers ............... G01N 1/26 700/276 |
| 2007/0272866 A1 | 11/2007 | Mengel et al. |
| 2008/0117066 A1* | 5/2008 | Kononov ............ G01N 33/0009 340/632 |
| 2009/0010801 A1* | 1/2009 | Murphy ............. B01D 46/0028 422/4 |
| 2009/0206657 A1 | 8/2009 | Vuk et al. |
| 2010/0101317 A1* | 4/2010 | Ashrafzadeh ....... G01F 23/0061 73/149 |
| 2012/0135512 A1* | 5/2012 | Vasylyev ............ G02B 19/0004 435/292.1 |
| 2012/0297868 A1 | 5/2012 | Elkins |
| 2012/0260719 A1 | 10/2012 | Schade |
| 2013/0293711 A1 | 11/2013 | Kapuria et al. |

* cited by examiner

MULTI-PARAMETRIC ENVIRONMENTAL DIAGNOSTICS AND MONITORING SENSOR NODE

TECHNICAL FIELD

The present invention relates to environmental quality monitoring and diagnostics systems and methods, and particularly to a multi-parametric environmental diagnostics and monitoring sensor node for environmental air quality monitoring and diagnostics that uses energy harvested concurrently from multiple renewable energy sources to power the sensor node.

BACKGROUND ART

The diversity and quantity of chemicals released into the environment has increased dramatically in recent years. These chemical emissions and their impacts are numerous and complex. These emissions have increased concerns about their adverse effects on their surroundings. These emissions have also resulted in increased regulatory and economic requirements for monitoring and treating the pollution. Conventional sensor devices for these emissions are small in size and communicate untethered over short distances. Typically, these conventional sensor devices consist of sensing units, data processing, and communication modules. In an attempt to support risk assessment and environmental sustainability, a large number of these conventional sensor devices can be deployed over large areas to collaboratively monitor the impact of human activity on air, water, soil and sediments by providing in situ, real-time data about the status of the environment, including bioavailability and mobility. Employing large numbers of these sensors can provide a finely resolved moment-by-moment analysis of changes in air quality, as well as potential exposure patterns. Large scale deployment of these conventional sensor devices, however, requires a large number of batteries, which may be toxic for the environment, and a large staff to maintain the sensor nodes for these environmental air quality monitoring systems.

Thus, a multi-parametric environmental diagnostics and monitoring sensor node solving the aforementioned problems is desired.

DISCLOSURE OF INVENTION

The multi-parametric environmental diagnostics and monitoring sensor node provides monitoring and diagnostics of a variety of different ambient environmental factors and is powered by multiple sources of renewable energy. Each sensor node includes a base having opposed upper and lower faces and an opening formed therethrough, a plurality of environmental condition sensors mounted on the upper face of the base, and a communications interface for communicating environmental data collected by the sensors to a base station. A controller or processor is also mounted on the upper face of the base. The environmental condition sensors are in communication with the controller. A power storage module is in communication with the environmental condition sensors and the controller. An external photovoltaic (solar) cell is mounted to the base and is exposed through the opening in the base. A cover is provided for covering the upper face of the base. The cover has a cover opening formed therein. An internal photovoltaic cell is mounted to the cover and is exposed through the opening in the cover.

The internal and external photovoltaic cells are each in communication with the power storage module for electrical charging thereof. In use, the base may be mounted on a support surface, such as a window in a room, such that the external photovoltaic cell is selectively exposed to light from an external source (e.g., sunlight) and the internal photovoltaic cell is selectively exposed to light from an internal source (e.g., artificial light from a light source in the room).

The power storage module may include a supercapacitor or the like, and may be powered by additional, auxiliary energy harvesting modules, such as a thermoelectric generator, a vibration transducer, and a radio frequency (RF) energy harvester. Preferably, the base is formed from a thermally conductive material, such as metal, so that the thermoelectric generator is driven by a temperature differential between the window and the internal environment of the room.

The sensor node has a power management system that includes a plurality of switches, such as MOSFET or CMOS switches, operating under control of the microcontroller for selectively charging the supercapacitor from the external photovoltaic cell, the internal photovoltaic cell, the thermoelectric generator, the vibration transducer and the radio frequency energy harvester, either separately or simultaneously.

These and other features of the present invention will become readily apparent upon further review of the following specification and drawings.

BEST MODES FOR CARRYING OUT THE INVENTION

Figure 1:
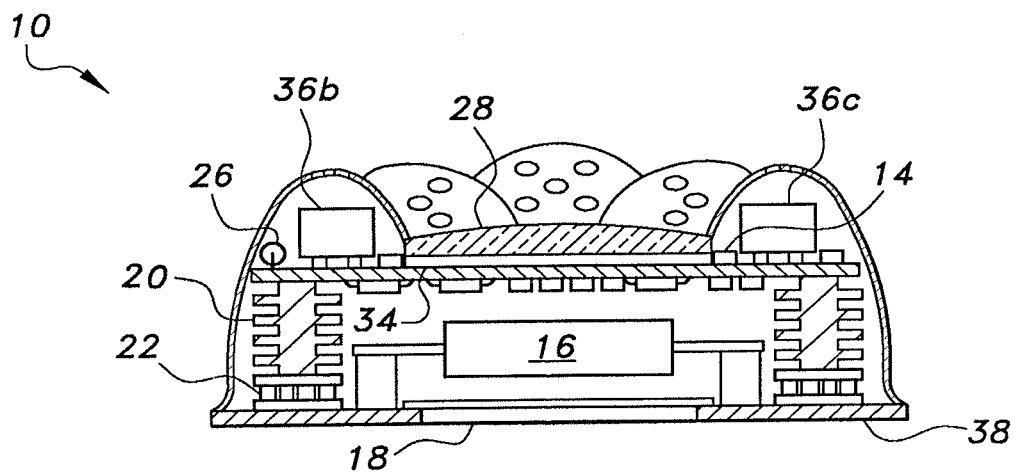
FIG. 1 is a side view in section of a multi-parametric environmental diagnostics and monitoring sensor node according to the present invention.
Figure 3:
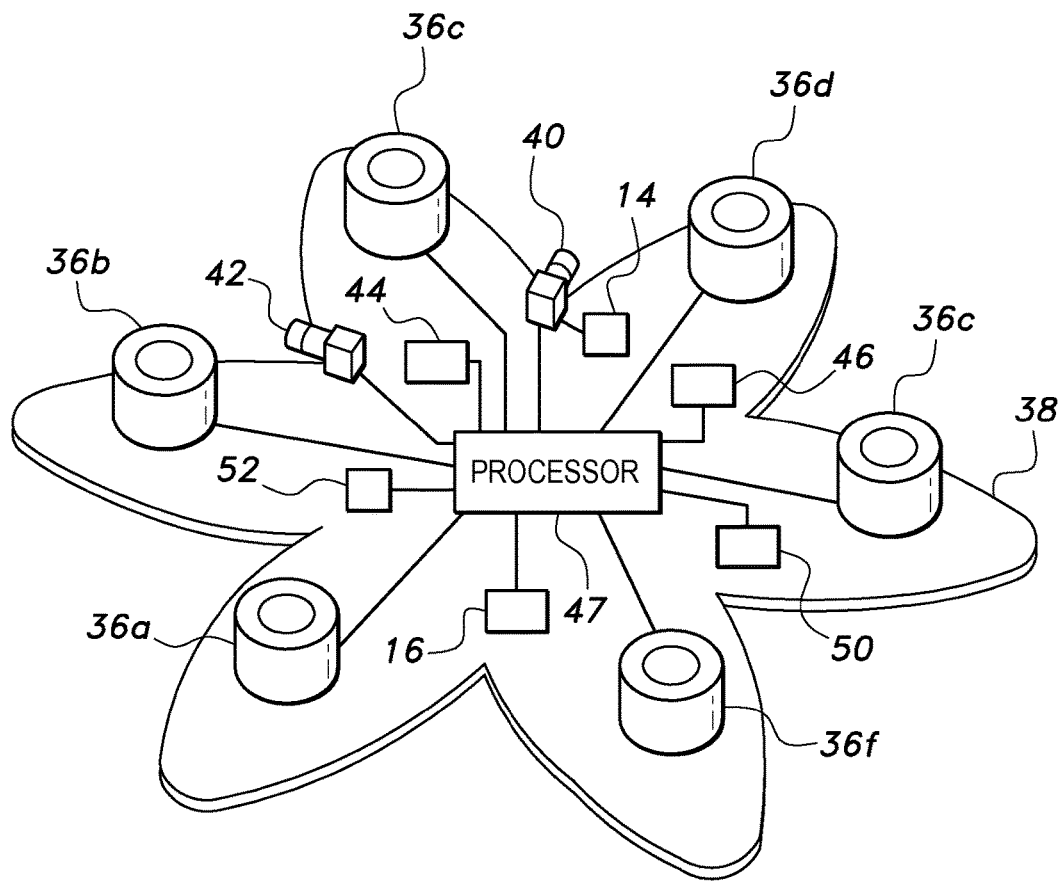
FIG. 3 is a diagram illustrating the layout of selected components of a multi-parametric environmental diagnostics and monitoring node according to the present invention.

The multi-parametric environmental diagnostics and monitoring sensor node 10 utilizes a combination of a variety of environmental power sources for powering a variety of different environmental sensors mounted on the node 10. As best shown in FIGS. 1 and 3, the multi-parametric environmental diagnostics and monitoring sensor node 10 includes a plurality of environmental sensors 36a, 36b, 36c, 36d, 36e and 36f operating together in a unitary system. For example, sensor 36a may be an electrochemical gas sensor for detecting and measuring levels of chlorine pollutants in the air, sensor 36b may be an electrochemical gas sensor for detecting and measuring levels of hydrogen sulfide pollutants in the air, sensor 36c may be an electrochemical gas sensor for detecting and measuring levels of carbon monoxide in the air, sensor 36d may be an electrochemical gas sensor for detecting and measuring levels of nitrogen dioxide pollutants in the air, sensor 36e may be an electrochemical gas sensor for detecting and measuring levels of nitrogen monoxide pollutants in the air, and sensor 36f may be an electrochemical gas sensor for detecting and measuring levels of ammonia pollutants in the air. It should be understood that any desired type of sensor may be utilized for detecting any desired type of pollutant, contaminant or other substance. Further, although six such sensors are shown mounted on a six-lobed base 38, it should be understood that any desired number of sensors may be used, and that the base 38 may have any desired overall configuration and relative dimensions.

As shown, the sensors 36a-36f are each in communication with a central processor 47. It should be understood that central processor 47 may be any suitable type of processor, programmable logic circuit, or any suitable type of controller or controlling circuitry, preferably a microcontroller. Power for the sensors 36a-36f and processor 47 is provided from a wide variety of sources, including a radio frequency (RF) harvesting module 14 in communication with an RF harvesting antenna 40 for harvesting radio frequency electromagnetic radiation in the environment and converting the RF into usable electricity, a mechanical resonator 16 for converting vibration into usable electricity, an outdoor photovoltaic cell 18 and an indoor photovoltaic cell 34.

Figure 2:
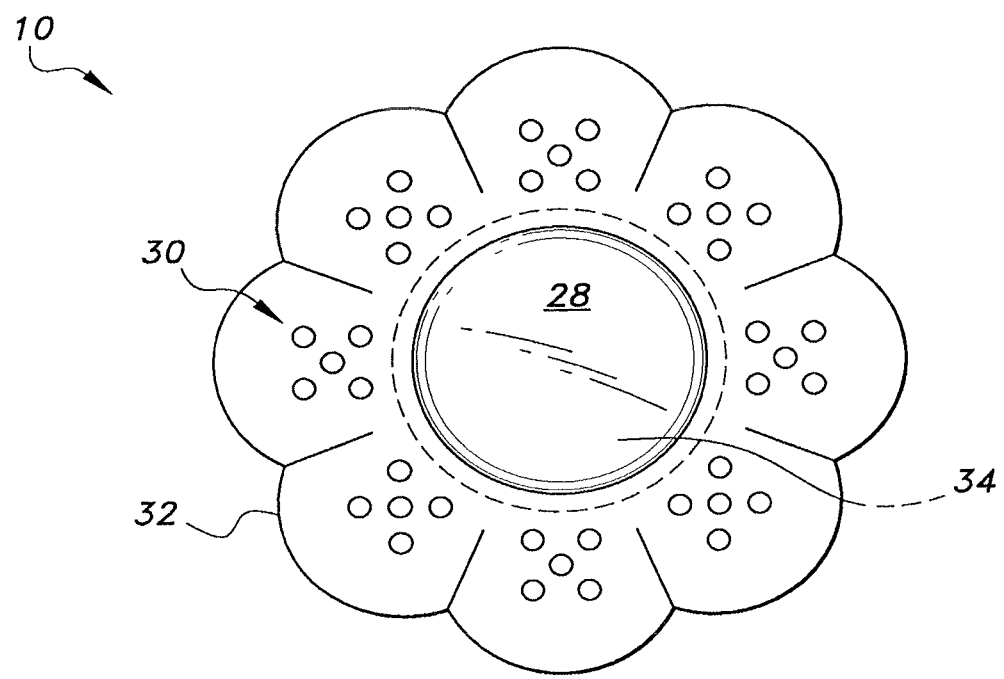
FIG. 2 is a top view of the multi-parametric environmental diagnostics and monitoring sensor node of FIG. 1.
Figure 4:
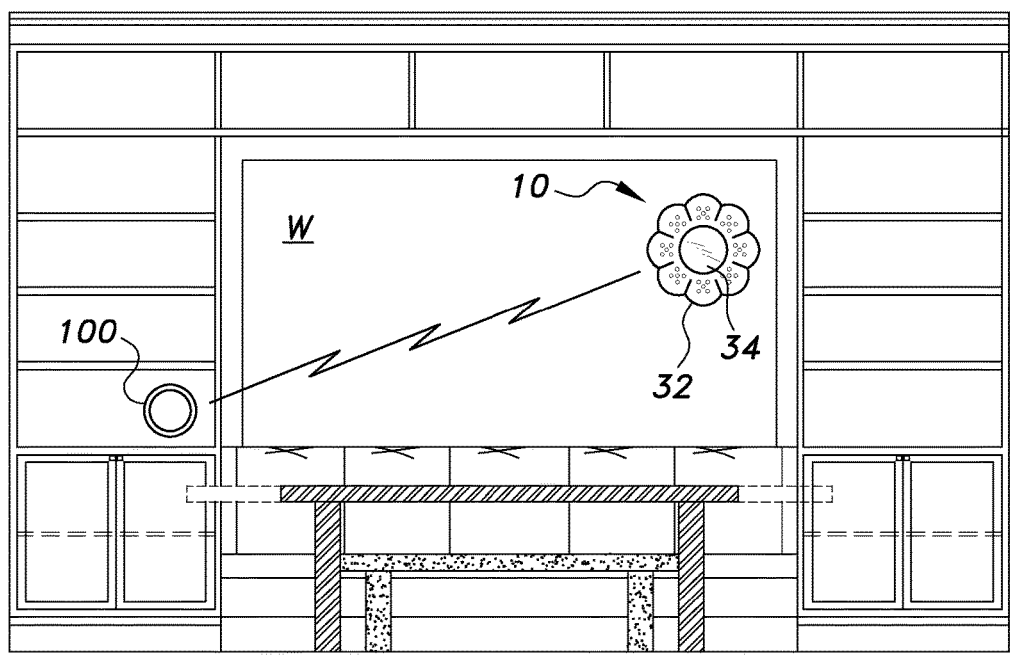
FIG. 4 is an environmental front view of a multi-parametric environmental diagnostics and monitoring sensor node according to the present invention, shown attached to an exemplary window.

As shown in FIG. 4, the base 38 of the multi-parametric environmental diagnostics and monitoring system 10 may be mounted to a window W such that cover 32, which covers the base 38 and the electronic modules mounted thereon, faces inwardly (i.e., towards the interior or indoors of the room containing the window W), and such that the external face of the base 38 faces the window W. This allows the outdoor photovoltaic cell 18 to be exposed to external environmental light for providing power, and the indoor photovoltaic cell 34, which is preferably mounted beneath lens 28 of cover 32, as shown in FIGS. 1 and 2, to be exposed to internal environmental light for providing additional power. Both the outdoor photovoltaic cell 18 and the indoor photovoltaic cell 34 are in communication with a solar power module 50. A solid state or electrolytic capacitor 52 or the like may further be provided for storing energy collected by the various sources of power. It should be understood that, in addition to, or instead of, capacitor 52, a suitable rechargeable battery or other electrical storage device may be used. Additional sources of power, such as thermoelectric generator 22, may be provided, along with any other suitable type of portable, environmental power harvester, such as piezoelectric or magnetic harvesters. Additionally, it should be understood that additional environmental sensors 44 may be provided, such as relative humidity, barometric pressure, lux, or temperature sensors.

As shown in FIG. 2, openings or apertures 30 are preferably provided in the cover 32, allowing environmental air to pass therein for contacting the sensors 36a-36f. As noted above, the overall configuration of the sensor node 10 and the cover 32 thereof are shown for exemplary purposes only, and the cover 32 may have any desired overall configuration or relative dimensions. Further, as shown in FIG. 4, the data detected and processed by the multi-parametric environmental diagnostics and monitoring system 10 may be transmitted wirelessly (via antenna 42 of FIG. 3) to a remote monitoring station 100. The remote monitoring station may be a remote computer, computer system, terminal, smart phone or the like, and may receive environmental air quality data from multiple sensor nodes. It should be further understood that the multi-parametric environmental diagnostics and monitoring sensor node 10 may be used in any location, whether indoors or outdoors, to monitor environmental conditions.

As shown in FIG. 1, a connector 20 is provided on the outer face of the base 38 for connecting the multi-parametric environmental diagnostics and monitoring sensor node 10 to other objects, such as a window W, along with a reed switch 26, which may magnetically trigger self-test functionalities of the multi-parametric environmental diagnostics and monitoring sensor node 10 without the need for an external mechanical button. Connector 20 may be any suitable type of connector or fixture, such as a magnetic base, for releasable connection to, for example, buildings, trains or bus windows. Alternatively, the connector 20 may be, for example, an adhesive connector, such as double-sided thermally conductive tape or the like.

It should be understood that the multi-parametric environmental diagnostics and monitoring sensor node 10 may be used in any desired location or environment for monitoring environmental conditions, and may be provided in a wide variety of shapes and sizes, allowing the sensor node 10 to be integrated into designs, logos, decoration and the like. The sensor node 10 may be used, for example, as a three-dimensional logo or piece of ornamentation in museums, in public administrations, governmental agencies, companies or the like. In the example of FIG. 4, the multi-parametric environmental diagnostics and monitoring sensor node 10 has a flower-type shape and is adhered or otherwise connected to a window W, and each lobe or "petal" of the flower contains one of the electrochemical sensors 36a-36f. In this exemplary arrangement, the central "pistil" of the simulated flower contains the indoor photovoltaic cell 34, covered by a lens 28.

The multi-parametric environmental diagnostics and monitoring sensor node 10 may be used to monitor environmental parameters at any desired indoor location such as, but not limited to, hospitals, museums, classrooms, offices, houses, museums, public administrations, governmental agencies, or company locations, as well as in the external environment around potential sources of pollutants, such as monitoring environmental parameters in, for example, stadiums, arenas, public areas, or industrial zones. The multi-parametric environmental diagnostics and monitoring sensor node 10 may also be used for collecting and analyzing data from industries, such as, but not limited to, agriculture, air transport, ground transportation, armed forces and security, biocides, catering and hospitality, construction, chemicals, diving, docks and ports, education, engineering, entertainment and leisure, explosives, fire/rescue services, food manufacture, footwear, gas supply, health services, laundries and dry cleaning, leather, local and/or federal government, mining, motor vehicle repair, nuclear, offshore oil and gas, paper, pesticides, law enforcement, printing, public services, quarries, railways, recycling, surface engineering, textiles or waste management.

It is important to note that the multi-parametric environmental diagnostics and monitoring sensor node 10 may be used either for continuous operations without user intervention, or may be used for operation at pre-determined intervals, or in response to an environmental cue. Multiple sensor nodes 10 may communicate with each other or with a central base station using a wireless computer network link, operating at any conventional low radio frequency, from approximately 3 kHz to approximately 30 GHz, and more preferably, at approximately 900 MHz. Time synchronization in communication networks may be important for basic communication and to facilitate group operations and improved network performance. Thus, each multi-parametric environmental diagnostics and monitoring sensor node 10 may use the RF energy from the 900 MHz signals to convey the minimum required energy to "wake up" and power up each multi-parametric environmental diagnostics and monitoring sensor node 10. Each multi-parametric environmental diagnostics and monitoring sensor node 10 may also use the RF energy from the 900 MHz signals to send broadcast network time synchronization pulses through tailored 900 MHz RF signal modulation to other remote sensor nodes 10.

With regard to processor 47, as noted above, any suitable type of controller, processor or control circuitry may be utilized. The control circuitry may include signal conditioning electronics designed around low-drift, low input bias current (for example, lower than approximately 90 pA) and ultra-low power operational amplifiers. The U.S. Environmental Protection Agency (EPA) designates a standardized air pollution level indicator, the Air Quality Index (AQI), which mainly refers to main parameters (together with particulate matter (PM) and carbon dioxide ($CO2$)) for carbon monoxide (CO), nitrogen dioxide ($NO_2$), and sulfur dioxide ($SO_2$). Thus, the control circuitry, in communication with sensors 36a-36f, should be able to detect these noxious gases in a timely and accurate manner. Most conventional sensors are gas specific and have usable resolutions under one part per million (ppm) of gas concentration matching these EPA requirements.

It should be understood that the control circuitry may include one or more microcontrollers, memory, power storage modules, data transmission modules and power management systems. The supercapacitor 52 may operate from 0.5 F at 5.5 VDC to 1.5 F at 5.5 VDC, and preferably 1 F at 5.5 VDC. The control circuitry may be powered from approximately 1.8 VDC to approximately 3.3 VDC, and more preferably at around 2.5 VDC. For example, in the conditioning electronics of the sensor signal, the microcontroller, and the transceiver may be powered at 2.5 VDC with a frequency dedicated to data transmission of approximately 433 MHz.

Power management modules of the sensor node 10 may include one or more energy converters, which may manage the charging and regulation of multiple outputs in the sensor node 10, in which the average power draw may be very low, but where periodic pulses of higher load current may be required. For example, the sensor node 10 power draw is extremely low most of the time, except for 433 MHz transmit pulses when the electronic circuitry is powered up.

The power management modules may include algorithms, such as custom sensor fusion algorithms, which may optimize the energy storing in the one or more capacitors, or any other conventional algorithm.

The lens 28 may include tailored two-dimensional (i.e., planar) or three-dimensional (i.e., spherical) lens profiles, which may be derived from conventional equations, such as the Luneburg equations, to focus light from all directions equally well on the central mono-crystalline solar cells. The lens 28 may increase the power harvesting capabilities of the indoor photovoltaic cell 34 and outdoor photovoltaic cell 18 by a factor from approximately two to approximately ten, and more preferably, approximately five. The lens 28 may focus an incoming plane wave to a point without any aberrations. Because of the preferred spherical symmetry of the lens 28, plane waves arriving from any direction may be focused to a point without any aberrations.

The multi-parametric environmental diagnostics and monitoring sensor node 10 may recover solar energy externally while concurrently recovering energy from indoor ambient light. The indoor photovoltaic cell 34 may be, for example, a thin-film amorphous silicon solar cell with a power density from approximately 0.1 $\mu W/mm^2$ to approximately 0.8 $\mu W/mm^2$, and more preferably, approximately 0.2 $\mu W/mm^2$. Under different illumination levels, the current/voltage ratios for the indoor photovoltaic cell 34 may be from approximately 200 lux (artificial light), 35 $\mu A$ at 4.8 VDC to approximately 1000 lux (artificial light), 165 $\mu A$ at 5.4 VDC, and more preferably about 400 lux (artificial light), 120 $\mu A$ at 5.2 VDC.

The outdoor photovoltaic cell 18 may be, for example, a thin-film amorphous silicon solar cell with power density from approximately 10 $\mu W/mm^2$ to approximately 80 $\mu W/mm^2$, and more preferably about 50 $\mu W/mm^2$. Under different illumination levels, the current/voltage ratios for the outdoor photovoltaic cell 18 may be from approximately 200 $W/m^2$ (natural light), 7 mA at 6 VDC to approximately 1000 $W/m^2$ (natural light), 33 mA at 6.5 VDC, and more preferably, about 600 $W/m^2$ (natural light), 20 mA at 6.3 VDC.

The thermoelectric generator (TEG) 22 is a device that converts heat (i.e., via temperature differences) directly into electrical energy, using, for example, the Seebeck effect. The TEG 22 may provide a high performance and highly efficient thermoelectric effect. The TEG 22, together with tailored heat sinks 24 directly connected to the TEG 22, has current/voltage ratios at 5° C. of approximately $I_{CC}$=47 mA at 75 mV. Power may be transferred to sensor node 10 using an external 1:100 step-up transformer. The TEG 22 current/voltage ratios at 15° C. may be about $I_{CC}$=127 mA at 200 mV (power may be transferred to sensor node 10 by an external 1:100 step-up transformer). The TEG 22 may include one or more high efficiency and/or highly integrated AC/DC converters adapted for harvesting surplus energy from extremely low input voltage sources. The TEG 22 may use, for example, two small external step-up transformers (ratio adopted 1:100), which may create an ultralow input voltage step-up DC/DC converter and power manager that can operate from input voltages of either polarity. This capability may enable energy harvesting from TEG 22 where the temperature differential across the TEG 22 may be of either known or unknown polarity. For example, multiple sensor nodes 10 may be stacked against window W, which may result in the external ambient temperatures being greater or lower than the indoor room temperature where the sensor node 10 is deployed.

It should be understood that the base 38 preferably has a central opening formed therethrough, allowing the outdoor photoelectric cell 18 to have direct exposure to the external source of light. Further, the base 38 is preferably made from metal, allowing for good thermal conductivity for operation of the TEG 22. With regard to the TEG 22, it should be understood that the TEG 22 may be used in a bipolar manner, i.e., if the temperature is colder on window W than inside the room (e.g., in the winter) or if the temperature is warmer on the window W than inside the room (e.g., in the summer). Further, when the TEG 22 detects a temperature differential greater than a pre-set threshold, the processor 47 may transmit an error or alarm signal to the remote monitoring station 100. It should be understood that any suitable number of thermoelectric generators 22 may be installed on the sensor node 10, connected in series with one another or the like. As will be described in greater detail below, a power management subsystem (shown in FIG. 9) may be used, allowing for processor-controlled switching between the energy harvesting modules. Such a switching system may be utilized when more than one thermoelectric generators 22 is utilized in order to implement the bipolar configuration described above, i.e., the thermoelectric generators 22 may be alternately arranged for each polarity of temperature gradient, and may be appropriately switched on and off, depending on the measured temperature gradient.

The RF harvesting module 14 may include on or more dedicated antennas, such as antenna 40. The one or more antennas 40, which may be able to receive and or transmit radio waves from one or more RF power sources operating at conventional low frequencies, from approximately 3 kHz to approximately 30 GHz, and more preferably at 500 MHz, 900 MHz or 2.4 GHz. The RF harvesting module 14 may convert RF energy to DC current. The RF energy harvester module 14 preferably has the ability to maintain RF-to-DC conversion efficiency over a wide range of operating conditions, including variations of input power and output load resistance. For example, the RF harvesting module 14 may not require additional energy-consuming circuitry for maximum power point tracking (MPPT), as may be required with other energy-harvesting technologies. The RF harvesting module 14 may maintain a high RF-to-DC conversion efficiency over a wide operating range that may enable scalability across applications and devices. The RF harvesting module 14 may further have a high efficiency conversion rate from approximately 20% to approximately 90%, and more preferably around 70% with ultra-low power consumption.

In addition to energy harvesting, the RF harvesting module 14 may be used to synchronize the sensor node 10, i.e., since the various sources of ambient energy cannot be controlled, the only way for a user to be completely sure that all of the energy harvesting nodes are operational (as opposed to, for example, it simply being nighttime and there being no solar radiation to harvest) and turned on is to transmit RF energy to the system, such as by a 915 MHz transmission sent by an external transmitter. When synchronization is needed, the external transmitter may send RF energy to all of the sensor nodes 10 at the same time, providing automated charging of the supercapacitor 52, power-ON and one-to-many device synchronization. The energy harvester module 14 may then be used both to periodically turn-on all the sub-systems, on demand, and also may receive synchronization data packets (i.e., packets used to reset the primary event counter in processor 47 so that all nodes have the same time base).

Conversion of RF energy into usable energy may be accomplished by receiving RF signals either from a dedicated RF transmitter(s) or from ambient sources (e.g., from mobile phones). The energy-harvesting module 14 converts RF energy to DC down to −12 dBm of input power over a frequency range from 1 MHz to 6 GHz, and provides an output up to 5 V to load via CMOS/MOSFET controlled switches (as discussed below with reference to FIG. 9) the 1 F supercapacitor 52 (or a tailored battery or the like).

The mechanical resonator 16 may be based on conventional piezoelectric technology (PZT) materials. The mechanical resonator 16 may include a vibration energy harvester, which may extract usable electrical energy from mechanical vibrations. The mechanical resonator 16 may be mounted in a tailored configuration, tuning the natural frequency of the harvester to match the vibration of one or more sources. For example, the power generated for the combination of resonance frequencies/seismic masses/accelerations at a frequency tuned to approximately 75 Hz, acceleration equal to approximately 0.5 g and seismic mass equal to approximately 15 g, may be approximately 2.3 mW. In another example, the combination of resonance frequencies/seismic masses/accelerations at a frequency tuned to approximately 130 Hz, acceleration equal to approximately 0.5 g and seismic mass equal to approximately 2.5 g, may be approximately 0.8 mW. In a further example, the combination of resonance frequencies/seismic masses/accelerations at a frequency tuned to approximately 180 Hz, acceleration equal to approximately 0.5 g and seismic mass equal to approximately 0 g, may be 0.6 mW. It should be understood that piezoelectric energy harvesting is well known, and any suitable type of piezoelectric system for harvesting energy from vibration, acoustic waves, seismic waves or the like may be utilized.

Figure 9:
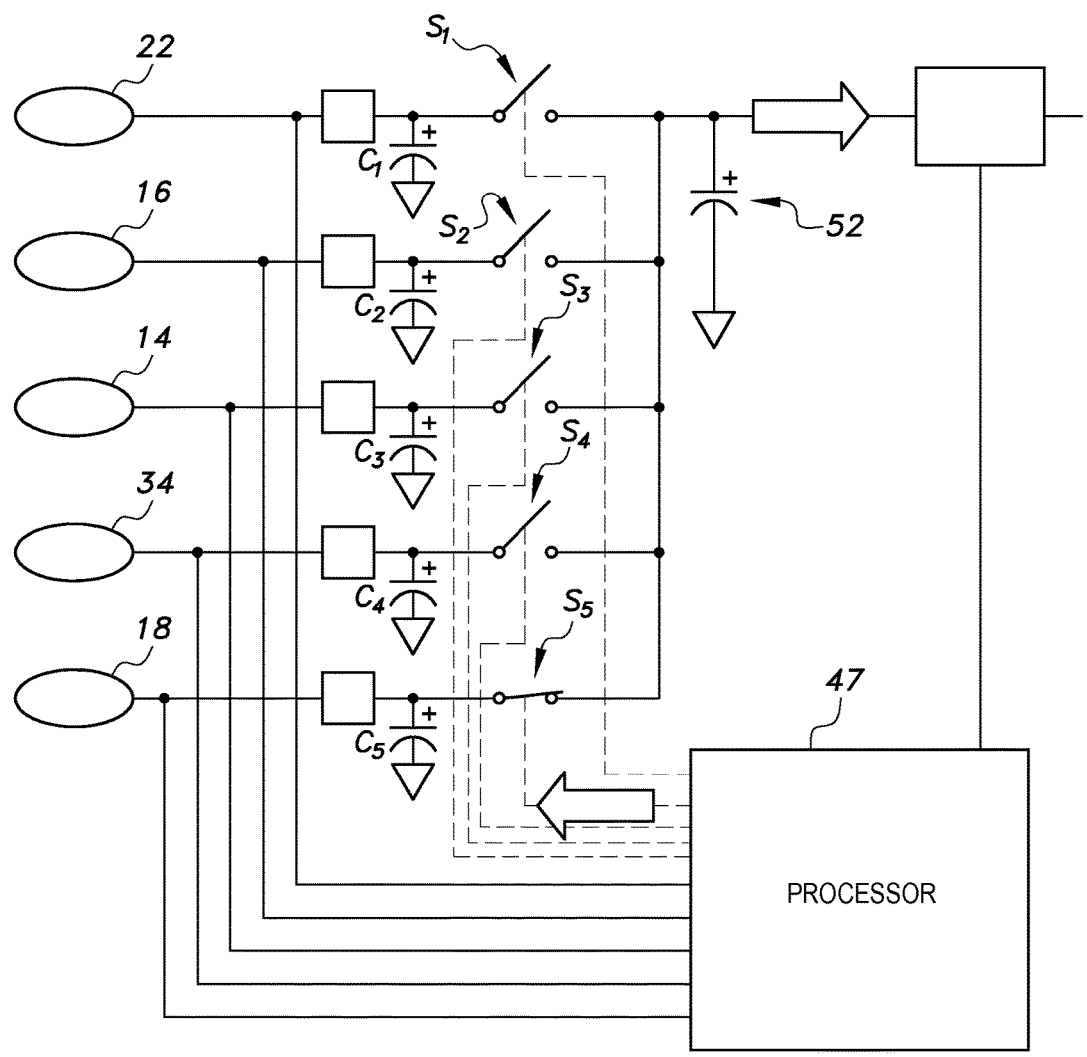
FIG. 9 is a schematic diagram of a power management circuit of a multi-parametric environmental diagnostics and monitoring sensor node according to the present invention.

As shown in FIG. 9, each of the energy harvesting modules 22, 16, 14, 34, 18 is connected, both each to the other and to supercapacitor 52, by respective MOSFET or CMOS switches $S_1$, $S_2$, $S_3$, $S_4$, $S_5$ (through appropriate capacitors $C_1$, $C_2$, $C_3$, $C_4$, $C_5$), under the control of the processor 47. This allows the backflow of the current to be set to zero when one, two or more of the various energy sources are active, while the remainder are inactive. By use of the MOSFET or CMOS switches under control of the processor 47, all configurations of energy harvesting are possible. For example, only the external photovoltaic cell 18 may be active, or both the external photovoltaic cell and the TEG 22 are active, but the other sources are inactive, etc.

Power in the sensor node 10 is approximately divided into 2% used for sensor warmup, 7% used in a "sleep mode", 16% dedicated for data processing, 40% used in sensor measurement, and 35% used in data transmission. The sensor node 10 and its electrochemical sensors 36a-36f may be kept off and turned on only periodically for energy-saving purposes. The electrochemical sensors 36a-36f may require a warmup time before the electrochemical sensors may be operational. Besides the warmup time, the wake-up latency and break-even cycle of the electrochemical sensors 36a-36f may be considered during power consumption calculations for the power management algorithms.

As noted above with reference to FIG. 4, the sensor node 10 may transmit environmental parameter data to a base unit 100 via a communication link. The communication link may use any conventional low frequency for communications between sensor node 10 and the base unit 100, typically from approximately 3 kHz to approximately 30 GHz, and preferably at approximately 433 MHz. The base unit 100 may be connected to an AC/DC power source. Alternatively, the base unit 100 may include one or more power harvesters, and may be powered by at least two, and more preferably, at least three, and most preferably, at least four harvesting modules simultaneously. As a further alternative, the base unit 100 may be powered by batteries. As noted above, the base unit 100 may be a computer or the like, preferably including at least a display, a communication module for accessing a communication network, a central processor, a system memory, and a system bus that couples various system components, including the system memory, to the central processor unit.

The base unit 100 may transmit instructions and updates to the sensor node 10 or receive data from the sensor node 10, and then send the data through a wireless link or network, or the like, to remote servers. These instructions may include a monitoring schedule, software and firmware updates for the sensor node 10, environmental parameter data, and other data required by the sensor node 10. Alternatively, each sensor node 10 may communicate directly with one or more remote computers or smartphones via the communication link.

The one or more remote servers may download historical data regarding the location from any source, such as the Internet or other databases. The one or more remote servers may analyze the data received from the base unit 100. This analysis may include: (i) gas sensor array cross-compensation, with the aim to increase measurement accuracy and long term stability avoiding uncorrected drift; (ii) correlation between gas sensor responses and temperature-RH %-barometric pressure levels with the aim to increase measurement accuracy; (iii) defining a geographic pollutants mapping, which may activate an early warning notification if pollutants trends differ from pre-set and/or pre-defined levels; or (iv) accessing though the Internet the weather forecast for one or more locations, which may include rain, wind, and barometric pressure. The weather forecast may help reduce the pollutants (by dilution) in the coming days, and at the same time, automatically adjust the early warning levels. As a further alternative, the analysis may create a feedback loop, in which historical and/or projected environmental data is used to determine a threshold for early warning notification of increased pollution levels at one or more locations by the sensor node 10. The one more remote servers may display the analysis of the data received from the base unit 100.

As noted above, the sensor node 10 may be deployed at any desired location. For example, one or more of the multi-parametric environmental diagnostics and monitoring sensor nodes 10 may be deployed in an underground transit system. In this example, the sensor nodes 10 are attached to one or more trains in the underground transit system using the connector 20. The sensor node 10 may continuously monitor the environmental parameter data of the surrounding environment at designated time intervals and/or designated locations. As described above, the sensor nodes 10 may transmit the environmental parameter data captured by sensor nodes 10 to base units 100 installed throughout the transit systems. In this example, the base units 100 may be installed at areas where trains stop, for example, train stations or train depots. Environmental parameter data received by the base units 100 may be transmitted to one or more remote computers or servers in real time for analysis. Alternatively, the environmental parameter data may be transmitted to one or more remote computers at designated intervals for analysis. In this example, the sensor node 10, using the mechanical resonator 16, may harvest piezoelectric energy from vibrations within the transit system, as well as thermal energy via TEG 22, simultaneously, to power the sensor node 10.

As a further alternative, the multi-parametric environmental diagnostics and monitoring sensor nodes 10 may be used in combination with a portable device, an appliance or the like, and the energy harvesting modules of the sensor node 10 may be used to provide power for the portable device, appliance or the like.

In order to study the effect of temperature on the electrochemical sensors of the multi-parametric environmental diagnostics and monitoring sensor node 10, two such multi-parametric environmental diagnostics and monitoring sensor nodes 10 were constructed, with the control circuitry built around a 16-bit PDIP PIC24 microcontroller featuring nanowatt extreme low power consumption (XLP) with a 500 nA "sleep mode" supply current. The microcontrollers had nine dedicated analog channels with internal 10 bits analog-to-digital converter (ADC) conversion successive approximation register (SAR). The gas sensor signal conditioning modules were developed with LT6004 operational amplifiers, manufactured by Linear Technology of Milpitas, Calif. The LT6004 amplifiers present an ultralow supply current (1 µA at 2.5 VDC) and low operating voltage, combined with desirable amplifier specifications, including an input offset voltage of 500 µV maximum with a typical drift of only 2 µV/° C., an input bias current of 90 pA maximum, and an open loop gain of 100,000.

Each of the multi-parametric environmental diagnostics and monitoring sensor nodes 10 were equipped with harvesting modules, including a TEG 22, an RF harvesting module 14, an indoor photovoltaic cell 34 and an outdoor photovoltaic cell 18. The harvesting modules were all configured to simultaneously charge a 1 F supercapacitor 52 at approximately 5.5 VDC, together with five sensor arrays based on two gas sensors (CO and $NO_2$), one temperature sensor, one humidity sensor (RH %) and a barometric pressure transducer.

Figure 5:
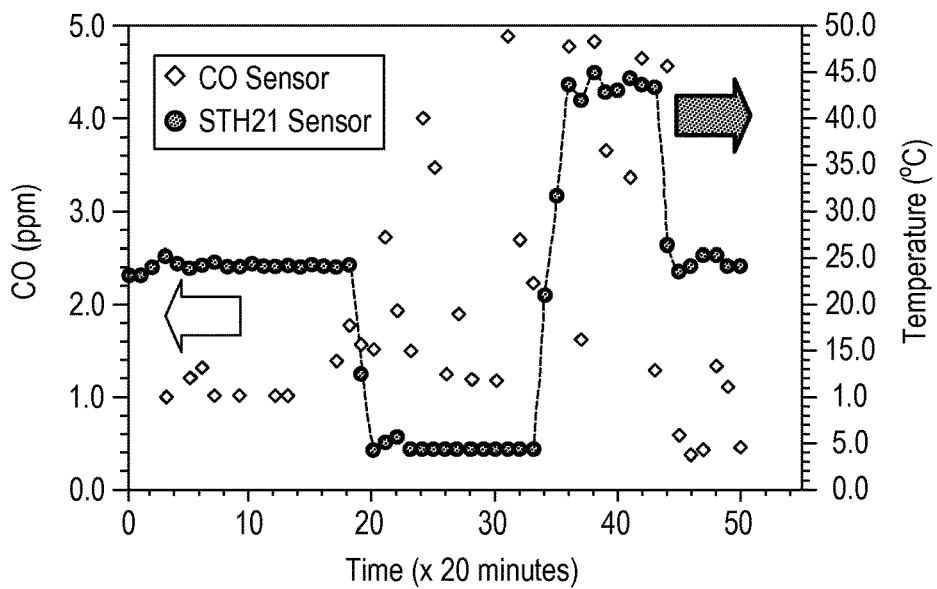
FIG. 5 is a graph comparing carbon monoxide monitoring and combined temperature and humidity monitoring of a multi-parametric environmental diagnostics and monitoring sensor node according to the present invention, both over time and for variations in ambient temperature.
Figure 6:
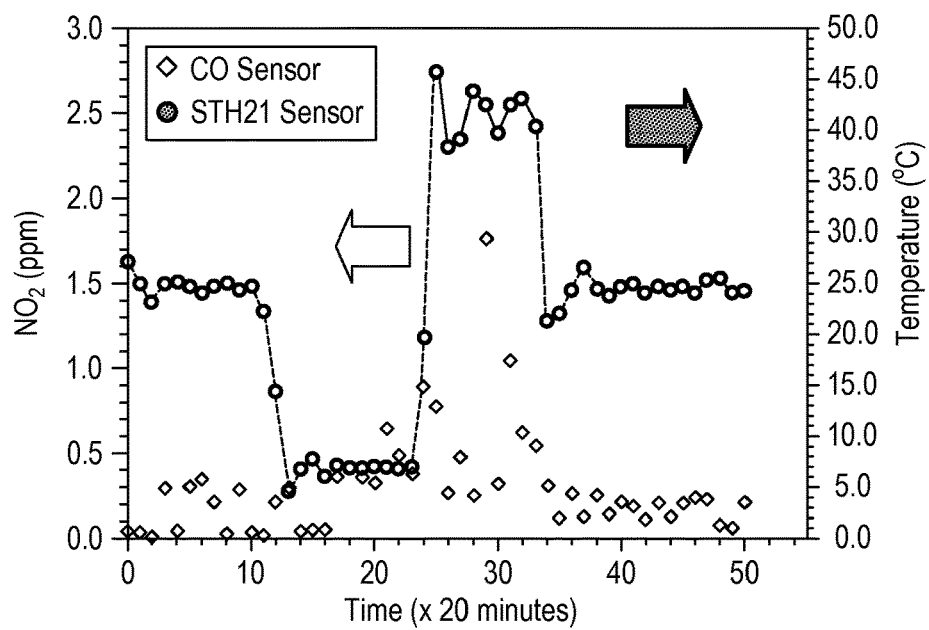
FIG. 6 is a graph comparing nitrogen dioxide monitoring and combined temperature and humidity monitoring of a multi-parametric environmental diagnostics and monitoring sensor node according to the present invention, both over time and for variations in ambient temperature.

The multi-parametric environmental diagnostics and monitoring sensor nodes 10 were deployed for approximately five months to numerous locations in Italy and in Doha, Qatar. During the five months, each of the multi-parametric environmental diagnostics and monitoring sensor nodes 10 were deployed under different conditions, including, but not limited to, variations in light emission, vibration levels, temperature gradients and RF radiation power. This test of the multi-parametric environmental diagnostics and monitoring sensor nodes 10 provided evaluation of how the five sensors responded to temperature variations in a thermal range of approximately +5° C. to approximately +50° C. The electrochemical sensors included an NE-CO carbon monoxide sensor (output current of 65 nA per 1 ppm of carbon monoxide) and an NE-$NO_2$ nitrogen dioxide sensor (output current of 690 na per 1 ppm of nitrogen dioxide), each manufactured by Shanghai Nemoto Electronic Technology Co., Ltd. of Shanghai, China. Additionally, an SHT21 digital humidity and temperature sensor (RH/T) was also utilized. FIG. 5 illustrates that the NE-CO sensor exhibited zero drift lower than approximately 5 ppm when compared with the temperature behavior. The NE-$NO_2$ sensor exhibited zero drift lower for approximately 1 ppm when compared with the temperature behavior, as illustrated in FIG. 6.

Figure 7:
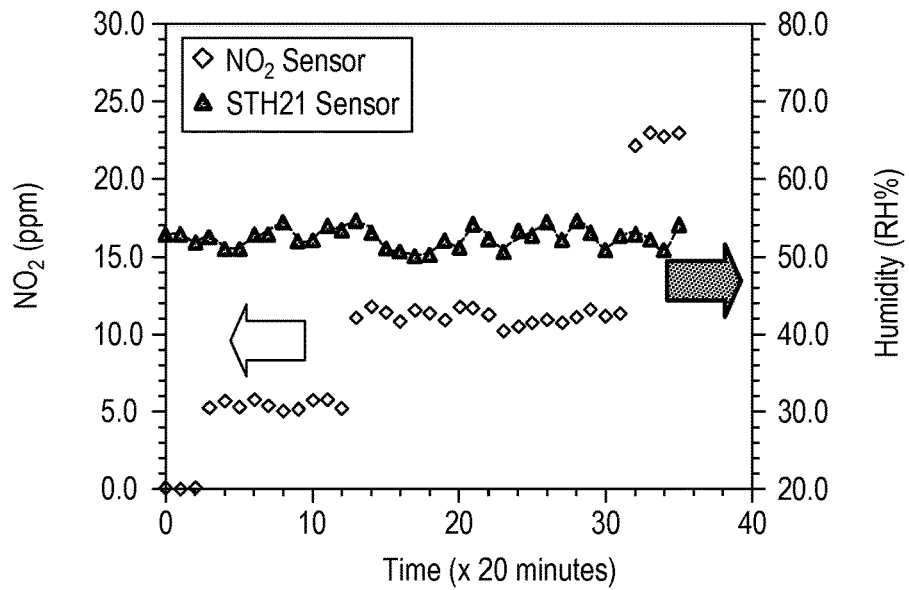
FIG. 7 is a graph comparing nitrogen dioxide monitoring and combined temperature and humidity monitoring of a multi-parametric environmental diagnostics and monitoring sensor node according to the present invention, both over time and for variations in ambient humidity.
Figure 8:
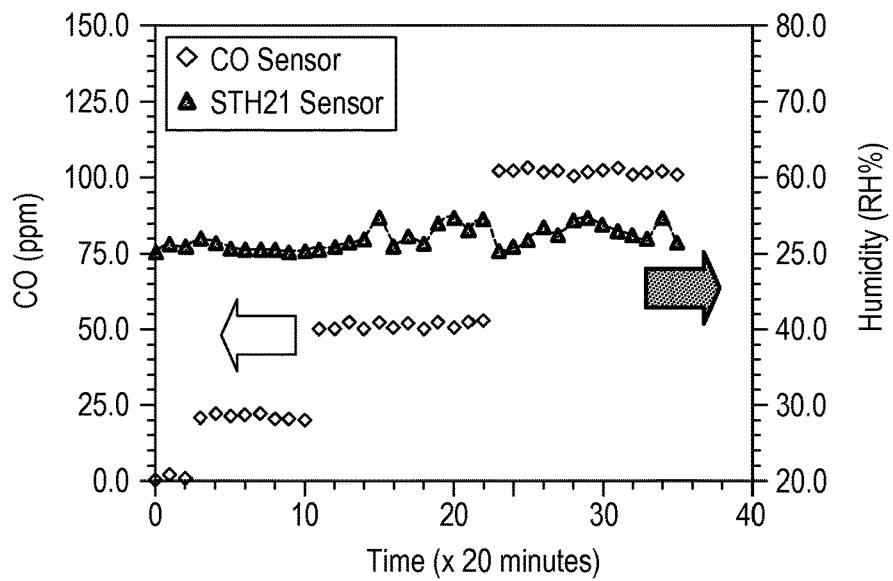
FIG. 8 is a graph comparing carbon monoxide monitoring and combined temperature and humidity monitoring of a multi-parametric environmental diagnostics and monitoring sensor node according to the present invention, both over time and for variations in ambient humidity.

The multi-parametric environmental diagnostics and monitoring sensor nodes 10 were also used to evaluate the effect of gas variation on the electrochemical sensors. In order to study the effects of gas variation on the CO and $NO_2$ sensors, the multi-parametric environmental diagnostics and monitoring sensor nodes 10 were separately deployed in a tailored test chamber. The levels of gas concentration in ppm were fixed using a mass flow controller connected to gas bottles with standard concentration (e.g., 10 ppm $NO_2$). The voltages obtained from the electrochemical sensors were received via 433 MHz wireless transmission in the receiving module 100 and stored by a main processing and control unit computer, which performed the data processing and data logging. The data was ultimately displayed and analyzed in a webserver, which also collected a historical evolution of the air quality in the monitored gas chamber areas to evaluate air quality trends. The results, displayed in a manner similar to those of FIGS. 5 and 6, but for gas variation, are shown in FIGS. 7 and 8.

Further, in order to evaluate power consumption of the electrochemical sensors, the multi-parametric environmental diagnostics and monitoring sensor nodes 10 were also deployed inside a location, at a window W (similar to the arrangement of FIG. 4). This arrangement allowed for evaluation of power consumption versus perpetual functionality of the sensor node 10. Table 1 below shows the energy budget recorded and associated with a fully operational remote multi-parametric environmental diagnostics and monitoring sensor node 10.

TABLE 1

Energy Budget of Multi-parametric Environmental Diagnostics and Monitoring Sensor Node

| Operation | Energy per day (J) |
| --- | --- |
| Sensor warmup (60 sec. every 20 min.) | 0.07 |
| Sensor measurement (2 sec. every 20 min.) | 2.16 |
| Data processing and storage (1 sec. every 20 min.) | 0.75 |
| Data transmission (0.6 sec. every 20 min.) | 1.55 |
| Sleep mode (19 min. every 20 min.) | 0.25 |
| Total system energy budget required by the IP prototype per day | ≈5 |
| Total energy recovered from external, low sunlight (average: 8 hours at 100 W/m², 6 hours at 50 W/m², 10 hours at 0 W/m²) | 250 |
| Total energy recovered from internal, artificial light (average: 8 hours at 200 lux) | 4.3 |
| Total energy recovered from temperature difference through the window (10 hours with 5° C. and 14 hours with 0° C.) | 6.2 |
| RF power sent (none) | 0 |
| Vibrations (none) | 0 |

It should be noted that the total energy harvested from the environment may exceed the total system energy budget required by the multi-parametric environmental diagnostics and monitoring sensor node 10 by almost a factor of approximately 1 to approximately 5, although typically approximately 2. This energy harvesting comes from renewable energy sources, such as internal artificial light and the thermoelectric effect. This factor may be increased from approximately 20 to approximately 80, though typically approximately, 50, when external light is used as the renewable energy source. In the example of Table 1, the multi-parametric environmental diagnostics and monitoring sensor node 10 was used with an operating cycle of once every 20 minutes. For data transmission, a medium-range transceiver, operating at 433 MHz, was included, allowing for transmission of data over a distance of approximately 500 m within line of sight, while dissipating 25 mW over a time interval of 0.6 seconds, thereby dissipating about 15 mJ per operation cycle.

It is to be understood that the present invention is not limited to the embodiments described above, but encompasses any and all embodiments within the scope of the following claims.

The invention claimed is:

1. A multi-parametric environmental diagnostics and monitoring sensor node, comprising:
   a base having opposed upper and lower faces and an opening formed therein;
   a plurality of environmental air quality sensors, each of the sensors having opposed upper and lower surfaces;
   a connector engaging each of the lower surfaces of the environmental sensors, wherein each of the connectors are mounted on at least one auxiliary harvesting module;
   a microcontroller mounted on the upper face of the base, the environmental air quality sensors being in communication with the microcontroller;
   a power storage module in communication with the environmental air quality sensors and the microcontroller;
   an external photovoltaic cell mounted within the base, the external photovoltaic cell being exposed through the opening in the base;
   a cover attached to the upper face of the base, the cover having an opening defined therein;
   the at least one auxiliary harvesting module in communication with the power storage module;
   an internal photovoltaic cell mounted on the cover, the internal photovoltaic cell being exposed through the opening in the cover; and
   a power management circuit connected to the power storage module, the power management circuit having a plurality of switches configured for selectively controlling communication between the power storage module and the external photovoltaic cell, the internal photovoltaic cell, and the at least one auxiliary harvesting module to charge the power storage module either separately or simultaneously from multiple sources, the internal and the external photovoltaic cells each being in communication with the power storage module for electrical charging thereof, the base being adapted for mounting on a support surface such that the external photovoltaic cell is selectively exposed to light from an external source and the internal photovoltaic cell is selectively exposed to light from an internal source.

2. The multi-parametric environmental diagnostics and monitoring sensor node as recited in claim 1, wherein said power storage module comprises a supercapacitor.

3. The multi-parametric environmental diagnostics and monitoring sensor node as recited in claim 2, further comprising a thermoelectric generator mounted on the upper face of said base and being in communication with the supercapacitor.

4. The multi-parametric environmental diagnostics and monitoring sensor node as recited in claim 3, wherein said base is formed from a thermally conductive material, such that the thermoelectric generator is driven by a temperature differential between the support surface and an internal environmental.

5. The multi-parametric environmental diagnostics and monitoring sensor node as recited in claim 4, further comprising a piezoelectric transducer in communication with said supercapacitor for charging said supercapacitor from electrical energy generated by vibrations.

6. The multi-parametric environmental diagnostics and monitoring sensor node as recited in claim 5, further comprising a radio frequency energy harvester in communication with said supercapacitor for charging said supercapacitor with electrical energy derived from radio frequency waves.

7. The multi-parametric environmental diagnostics and monitoring sensor node as recited in claim 1, wherein each of the switches comprises a CMOS switch.

8. The multi-parametric environmental diagnostics and monitoring sensor node as recited in claim 1, wherein each of the switches comprises a MOSFET switch.

9. The multi-parametric environmental diagnostics and monitoring sensor node as recited in claim 1, further comprising a lens covering said internal photovoltaic cell.

10. The multi-parametric environmental diagnostics and monitoring sensor node as recited in claim 1, wherein said cover has at least one aperture formed therein above each of the environmental air quality sensors to expose the sensors to ambient environmental air.

11. The multi-parametric environmental diagnostics and monitoring sensor node as recited in claim 1, wherein said at least one auxiliary harvesting module is selected from the group consisting of a thermoelectric generator, a piezoelectric transducer, and a radio frequency energy harvester.

* * * * *